(12) United States Patent
Matsuda

(10) Patent No.: US 6,977,231 B1
(45) Date of Patent: Dec. 20, 2005

(54) SUTURABLE ADHESION-PREVENTING MEMBRANE

(75) Inventor: Kazuhisa Matsuda, Osaka (JP)

(73) Assignee: Nipro Corporation, Osaka (JP)

( * ) Notice: Subject to any disclaimer, the term of this patent is extended or adjusted under 35 U.S.C. 154(b) by 520 days.

(21) Appl. No.: 09/489,473

(22) Filed: Jan. 21, 2000

(30) Foreign Application Priority Data

Jan. 21, 1999 (JP) .................................. 11-012625
Mar. 29, 1999 (JP) .................................. 11-085477

(51) Int. Cl.$^7$ .......................... B32B 5/24; A61B 17/04; A61F 13/00
(52) U.S. Cl. ....................... 442/370; 442/373; 442/374; 442/123; 606/228; 606/229; 606/230; 606/231; 424/422; 424/423
(58) Field of Search ............................... 442/370, 374, 442/373, 123, 97, 153

(56) References Cited

U.S. PATENT DOCUMENTS

| | | | | |
|---|---|---|---|---|
| 5,171,273 A | * | 12/1992 | Silver et al. ................... | 623/13 |
| 5,201,745 A | | 4/1993 | Tayot et al. ................... | 606/151 |
| 5,514,181 A | * | 5/1996 | Light et al. ................... | 623/13 |

FOREIGN PATENT DOCUMENTS

| EP | 0 645 149 A1 | 3/1995 |
|---|---|---|
| EP | 0 639 523 A2 | 1/1996 |
| EP | 0 943 346 A1 | 9/1999 |
| JP | 7-116242 A | 5/1995 |
| JP | 7-178131 A | 7/1995 |
| JP | 8-52204 A | 2/1996 |
| JP | 10-113384 A | 5/1998 |
| JP | 11-033104 A | 2/1999 |
| WO | WO 89/08467 | 9/1989 |
| WO | WO 95/18638 | 7/1995 |
| WO | 98/22157 A1 | 5/1998 |

OTHER PUBLICATIONS

Database WPI, Section Ch, Week 199828, Derwent Publications Ltd., London, GB, AN 1998-315641, XP002136590 & JP 10 113384 A

* cited by examiner

Primary Examiner—Terrel Morris
Assistant Examiner—A B Sperty
(74) Attorney, Agent, or Firm—Kubovcik & Kubovcik

(57) ABSTRACT

A suturable adhesion-preventing membrane has high suture strength, good biocompatibility, decomposition and absorption in a living body, sufficient adhesion-preventing effect, and desirable guided tissue regeneration. The membrane is composed of at least one non-woven fabric layer made of collagen fibers, or a laminated membranous substance consisting of at least one non-woven fabric layer made of collagen fibers and at least one sponge layer made of collagen, and a coating layer of gelatin or hyaluronic acid on the surface or surfaces of the above membrane. Preferably, the membrane comprises one to six compressed cross-linked collagen non-woven fabric layers wherein a layer has a fibers having a fiber diameter of 0.05 mm to 1.0 mm, a bulk density of $5.0 \times 10^{-4}$ to 5 g/cm$^3$ and a thickness of 0.1 mm to 50 mm, and a coating layer containing gelatin or hyaluronic acid and having a thickness of 0.05 mm to 20 mm, wherein the coating layer covers one or both sides or a part or whole of the surface of the membrane.

14 Claims, 6 Drawing Sheets

Example 6  Flow chart    ( five-layer membrane :
gelatin / collagen sponge / collagen non-woven fabric / collagen sponge /gelatin )

continue to next page

Example 7  Flow chart  ( six-layer membrane : hyaluronate sponge / collagen sponge / collagen non-woven fabric / collagen sponge / hyaluronate sponge )

continue to next page

US 6,977,231 B1

SUTURABLE ADHESION-PREVENTING MEMBRANE

FIELD OF THE INVENTION

This invention relates to a suturable adhesion-preventing membrane, and more particularly to a suturable adhesion-preventing membrane based on collagen and used for guided tissue regeneration. Even more particularly, the invention relates to a membrane that is utilized in a living body as an adhesion-preventing membrane for a prosthesis; to repair, augment or replace parts of tissues and organs that have been destroyed or weakened by disease or trauma or surgical operation such as abdominal wall defects or excised, transected, ablated or resected sites in tissues within a living body such as the pleura, pericardium, cerebral dura mater and chorion, and various organs. The membrane of the present invention is characterized by, in particular, being suturable, having good biocompatibility, and further, promoting tissue regeneration.

BACKGROUND OF THE INVENTION

In various surgical operations, an ablation of affected parts, a repair of damaged sites and surfaces or the like is very often conducted. Especially, in the surgical operations for various organs such as the lungs, heart, liver, brain, digestive organs and gallbladder, unless the resected site or defective part of the organs or the like is replaced or repaired or augmented (i.e., compensated) with a membranous substance covering the tissue of such organs, the fundamental functions of the organ will be damaged in many cases. If the treatment is not completely performed, the patient will die due to a malfunction of the organ or, even if the patient passes the crisis, an often observed tendency is that the prognosis is quite bad. Also, with respect to an insufficient suture fixation of the membranous substance in a prosthetic or compensated part, even if the function of the treated organ itself manages to be maintained, body fluids, digestive juices or contents which are exuded or leak from the organ may cause infection, or cause an attack or an erosion of other organs to eventually jeopardize life.

Further, there happens highly frequently an adhesion of the membranous substance at these prosthetic or compensated parts, and consequently, a malfunction of the organ may be induced in the course of time. In order to solve such problems, membranous substances or adhesion-preventing membranes made of various materials have been developed to cover the organ or the tissue of the organ.

Conventionally, a surgical wound dressing material is known in which a non-woven fabric layer made of collagen fibers is treated with aldehydes to have water resistance and the fibers are bonded mutually with collagen (Japanese Unexamined Patent Publication No. 141190/1975). However, because the surface of the dressing material is treated with a cross-linking agent, the material has inferior biocompatibility or is inferior in guiding tissue regeneration. Further, it is uncertain whether the dressing material can function to have sufficient suture strength or prevent an adhesion of a wound although it covers the wound.

In the above conventional technique, the adhesion-preventing membrane exhibits insufficient adhesion-preventing effects, suture strength, biocompatibility and decomposition and absorption capability in a living body, and particularly, the membrane can not simultaneously exhibit these characteristics. Therefore, the aim of the present invention is to resolve simultaneously the conventional problems of adhesion-preventing membranes that include insufficient suture strength, insufficient biocompatibility or decomposition and absorption capability in a living body, and insufficient adhesion-preventing effects as well.

The present inventor has already proposed as an improved medical membrane utilizing only animal collagen, a medical collagen membrane of non-woven fabric layer which comprises cross-linked collagen in which at least one surface of a membrane is covered with a collagen coating (Japanese Patent Application No. 264891/1998). Because the surface of the membrane is not cross-linked with a cross-linking agent, the membrane is superior in biocompatibility, guiding tissue regeneration and the like as compared to a surgical wound dressing material in which a non-woven fabric layer made of collagen fibers is treated with aldehydes to have water resistance and the fibers are bonded mutually with collagen (Japanese Unexamined Patent Publication No.141190/1975). Also, another characteristic of the membrane is to have a wide variety of applications for surgical procedures as in, particularly, compensation or prothesis of various organs, since the membrane can be fixed directly to the organs by means of a suture. Additionally, the membrane especially has strength enough to withstand suture fixation compared to a patch for visceral surgery which is comprised of two layers of (1) porous fibrous collagen layer and (2) collagen and/or a gelatin membrane (Japanese Patent No. 2775115). Therefore, it is possible for the membrane to be fixed more firmly to application sites with a general and inexpensive surgical suture thread as compared to fixation with only a biological adhesive, and a wide range of surgical applications are characteristically provided.

However, the above improved membrane has a difficulty in obtaining a sufficient adhesion-preventing property because the raw material of the membrane is collagen derived from an animal, which promotes adhesion, proliferation and extension of cells. Therefore, it is an object of the present invention to provide a suturable and adhesion-preventing membrane for guided tissue regeneration which is superior in suture strength, biocompatibility and guiding tissue regeneration, and further has an adhesion-preventing property.

SUMMARY OF THE INVENTION

As a result of intensive research to solve such problems, the present inventor has found that when at least one non-woven fabric layer made of collagen fibers is used to form a membrane, or a non-woven fabric layer made of collagen fibers and a sponge layer made of collagen are used to form a membranous substance having a laminated structure, and a coating layer containing gelatin or hyaluronic acid is provided on the surface of the membrane or the membranous substance, a desired membrane is formed that has sufficient suture strength, good biocompatibility, a property for promoting tissue regeneration and a sufficient adhesion-preventing effect, thus completing the present invention.

The present invention is directed to a suturable adhesion-preventing membrane for guided tissue regeneration comprising a membrane having at least one non-woven fabric layer made of collagen fibers, or a laminated membranous substance having at least one non-woven fabric layer made of collagen fibers and at least one sponge layer made of collagen, characterized in that at least one surface of the membrane or laminated membranous substance is provided with at least one coating layer containing gelatin or hyaluronic acid.

DETAILED DESCRIPTION

Figure 1:
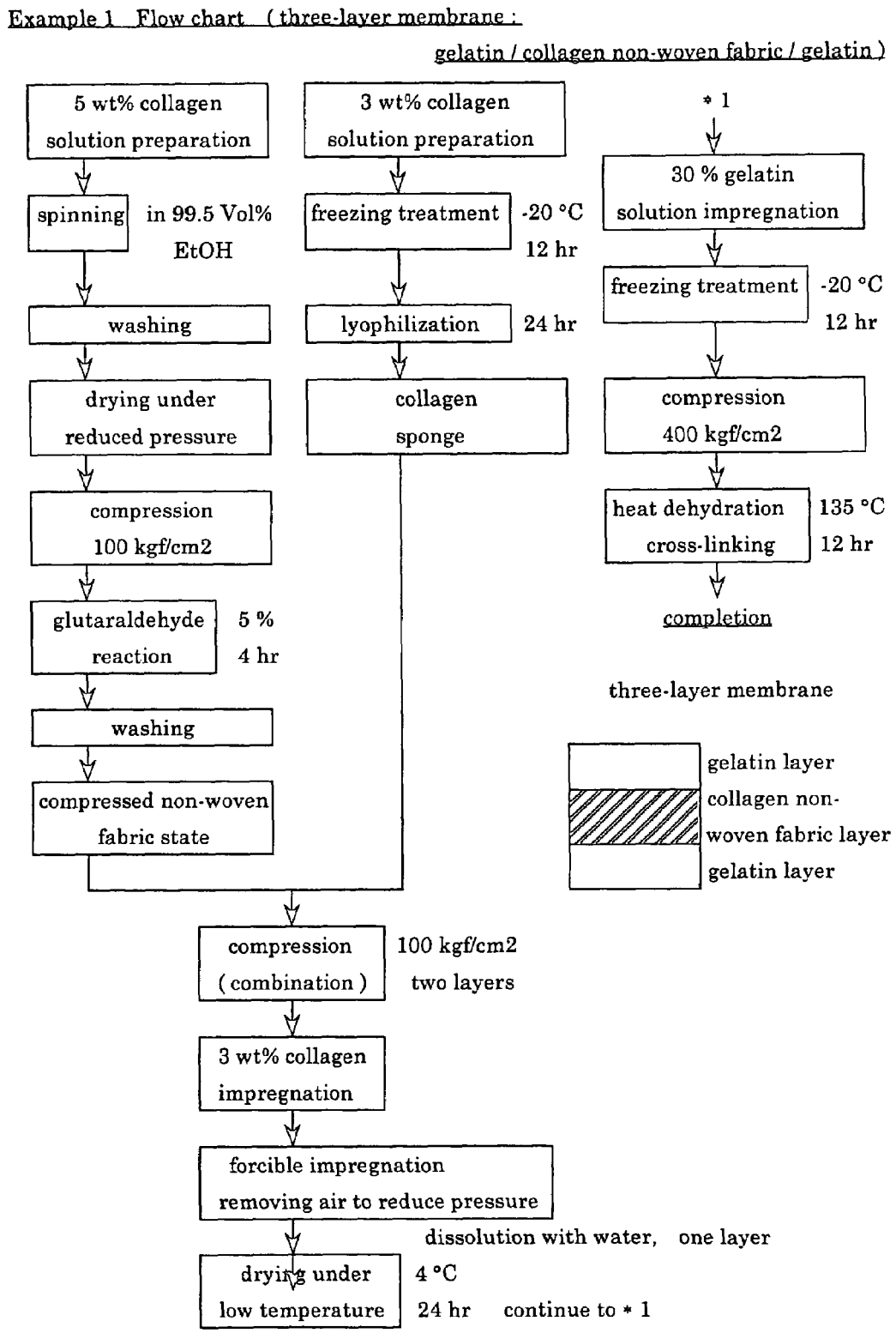
FIGS. 1 to 4 are flow charts illustrating the processes described in Examples 1, 2, 6 and 7, respectively, for preparing suturable adhesion-preventing membranes of the present invention.

Now, the most simple and effective way to prevent adhesion is to avoid contact between tissues damaged by injury or deficit and other tissues that have possibility of physically contacting the damaged tissue by means of barrier. However, a barrier made of synthetic fibers and the like causes various disadvantages such as excessive calcification, xenobiotic reaction, an inflammatory response and the like because of insufficient biocompatibility. Accordingly, the barrier material itself should not mediate the adhesion of damaged or defective tissues to other tissues corresponding thereto. Hyaluronic acid, gelatin and the like are enumerated as materials that satisfy such a requirement. Both hyaluronic acid and gelatin are capable of being treated as viscous aqueous solutions and utilized as a gel by various processing methods.

As these materials are extracted and purified from mainly the living body of an animal or the like, their good biocompatibility has already allowed them to be put to practical use in medical drugs and other various medical fields. Further, when the materials are implanted in a living body, gelatin or hyaluronic acid molecules are continuously released during decomposition and absorption processes, to exert viscosity and maintain the hydrophilic property. As a result, even if the materials are in contact with parts of the damaged or deficient tissues, they also have a characteristic to make it difficult to cause physically binding or adhesion.

Exemplified as techniques to produce, by applying these characteristics, an adhesion-preventing membrane, medical material or the like utilizing hyaluronic acid are ones disclosed in Japanese Unexamined Patent Publication Nos. 73103/1994 and Japanese Examined Patent Publication No. 30124/1995, Japanese Registered Patent No. 2670996, Japanese Unexamined Patent Publication Nos. 333402/1986 and 234864/1986, Japanese Registered Patent No. 2648308, Japanese Unexamined Patent Publication Nos. 157378/1996, 296005/1997, 102002/1995, and 509386/1995 and the like. However, a technique to provide not only an adhesion-preventing effect but also induction of tissue regeneration and mechanical strength sufficient to withstand suturing can not be found in the disclosed techniques, nor in other existing techniques.

Examples of techniques that utilize gelatin with the expectation of an adhesion-preventing effect, as in the case where hyaluronic acid is used, include ones disclosed in Japanese Unexamined Patent Publication Nos. 103479/1997 and 52204/1996. However, similar to the technique using hyaluronic acid, neither of the techniques disclosed in these publications has succeeded in providing a medical material that can concurrently satisfy the three requirements consisting of adhesion-preventing effect, mechanical strength capable of suture fixation and guiding tissue regeneration.

The term "suturable" in the present invention means such a state that a membrane can be fixed at a part of the membrane, for instance, two or more points thereof to an implanted part in a living body, for example, defective sites in the pericardium, cerebral dura mater, pleura, intestinal chorion and the like, or a resected part in the lungs, liver or the like, using a general suture thread for surgery. Further, it also means that the membrane can be maintained in a state that the membrane does not easily deviate, drop, or move from the suture-fixed position or deform for a certain period of time.

The term "guided tissue regeneration" means that the adhesion-preventing membranes transplanted into defective sites in a tissue or organ have a property to induce regeneration of the tissue. Specifically, such property refers to a state that natural healing and a regeneration process take place smoothly without showing an inhibition of normal regeneration of body tissues, which is often observed when using an artificial composition such as a synthetic high molecular compound.

The term "biocompatibility" in the present invention means the degree of immunological and histological reactions in a living body when an artificial product is implanted into the body and is determined by an inflammatory response or the like observed by the naked eye.

The term "adhesion" means an agglutination or adhesion between organs or tissues that should be essentially separated from each other. This adhesion is determined by observation with the naked eye.

The adhesion-preventing membrane in the present invention does not contain any synthetic material such as synthetic fibers, but uses as main raw materials collagen and gelatin, or collagen and hyaluronic acid, which are materials derived from an animal, processes them into a form of a non-woven fabric or sponge, and layers the processed materials to provide a laminated structure of, mostly, 2 to 10 layers, preferably 3 to 5 layers.

In the adhesion-preventing membrane, it seems that the non-woven fabric layer mainly provides sufficient suturable membrane strength, the collagen sponge layer mainly provides biocompatibility and promotion of tissue regeneration, and the coating layer formed from gelatin or hyaluronic acid exerts biocompatibility and an adhesion-preventing effect with surrounding tissues.

The adhesion-preventing membrane of the present invention is entirely composed of collagen and gelatin or hyaluronic acid each of which is derived from an animal, so that it is excellent in compatibility and, moreover, can be gradually decomposed and absorbed in a living body to be totally decomposed and absorbed where it is. In the decomposition and absorption process, the collagen sponge layer mainly exerts characteristic properties of collagen, such as hemostatic reaction and adhesion, proliferation and extension of cells, thereby promoting tissue regeneration in a tissue or organ where the membrane is implanted.

Also, the collagen non-woven fabric layer remains as a basis to compensate, for prosthesis, or to seal defective parts or the like in a living body until the parts complete regeneration of the tissue. The collagen non-woven fabric layer maintains its strength for a certain period after the suture fixation of the membrane, and then is decomposed and absorbed similar to the collagen sponge layer. Certainly, as this non-woven fabric layer is also composed of collagen, the layer can not only maintain its strength but can also significantly exhibit characteristics similar to the above collagen sponge. Further, the outermost layer containing gelatin or hyaluronic acid can prevent adhesion between damaged or defective parts and surrounding tissues, owing to its viscosity and sustained-release action.

Incidentally, the prevention of this adhesion lasts for a period during which tissues of the damaged or defective parts are regenerated and healed to an extent that adhesion between the tissues thereof and the surrounding tissues does not take place under the natural state. Since the adhesion-preventing membrane in the present invention is especially capable of being sutured, it can be directly fixed to a defective or damaged part in a living body. Therefore, it is possible to certainly separate a part to be adhered and a defective or damaged part and exert a good adhesion-preventing effect without moving, dropping out or deviating from the implanted part in a living body, which property has been observed in conventional adhesion-preventing membranes.

Representative collagen used for the present invention includes solubilized collagen such as enzyme solubilized collagen, acid solubilized collagen, alkali solubilized collagen or neutral solubilized collagen. The solubilized collagen is one that is solubilized with a proteolytic enzyme, for example, pepsin, trypsin, or with an alkali, and is obtained by performing, at the same time as solubilization, a treatment for removing telopeptide, which is an antigenic determinant of collagen. Usually, atelo-collagen applicable for medical use is especially suitable. The solubilized collagen can be readily obtained from animals by following publicly known techniques (Japanese Examined Patent Publication Nos. 15033/1969, 259839/1968, 27513/1968 and others).

Further, the source of the collagen used in the present invention is not specially limited, but generally includes bovines, swine, fowls, fishes, lapin, ovine, urine and humans. The collagen is produced from skin, tendon, bone, cartilage, organs and the like of these sources by means of various known extraction methods. Additionally, no particular limitation is put on collagen that can be classified into type I, type III or the like, but type I is most suitable from the view of handling. The solvent to solubilize the collagen is preferably water from the view point of handling.

Usual gelatin according to the Pharmacopoeia of Japan is usable.

Either one of hyaluronic acids derived from animals or from bacterium may be used but hyaluronic acid of medical grade is particularly suitable.

In order to obtain the non-woven fabric layer having sufficient suturable membrane strength, the above collagen solution is extruded into a coagulating bath to form fibers, and the fibers are crossed over one another in multiple layers at the bottom of the coagulating bath. Otherwise, the extruded fibers are wound on a plate in a certain direction to form a non-woven fabric layer having parallel lines of fibers. A fibrous aggregation in which the fibers have a diameter of 5 $\mu$m to 1.0 mm, preferably 10 $\mu$m to 1.0 mm, and more preferably 20 to 300 $\mu$m, is obtained. The bulk density (fiber density) of the fibrous aggregation is $5\times10^{-4}$ to 5 g/cm$^3$ preferably $1.0\times10^{-3}$ to 2.0 g/cm$^3$. That is, the above solubilized collagen solution is continuously wet spun, and the long fibers obtained are transferred to an appropriate vessel, and disposed to cross over one another but not in a single direction, for example, at approximately a 90° angle.

Alternatively, the long fibers continuously extruded through the orifices and coagulated in the spinning bath may be wound on a plate in a certain direction to form a non-woven fabric having parallel lines of fibers.

Then, non-woven fabric (fibrous material) is obtained which is made flocculent by vacuum drying, natural drying, low-temperature drying, blast drying or the like. It is important for the collagen to be dried at a denatured temperature or lower of the used collagen in each drying method in order to prevent denaturing of the collagen. Therefore, the temperature is preferably within a temperature range of about 35 to 45° C., which depends on the types of used collagen. Low-temperature drying or vacuum drying is especially preferable.

In another way, a fibrous material having short staples is manufactured in a method of either continuous spinning or non-continuous spinning, in which the fiber obtained is cut after intermittent extruding of the non-continuous spinning, or usual continuous spinning. It is also possible to obtain the non-woven fabric (fibrous material) by drying the staples, in a uniformly dispersed state in an appropriate size of vessel, through vacuum drying, natural drying or the like.

The concentration of collagen solution used for spinning is optional depending on the type of collagen used, and any concentration is useful if it is spinnable. Usually, the concentration is 0.1 to 20 wt %, of which a concentration of about 1 to 10 wt % is especially suitable for wet spinning. Further, the extruding speed of solubilized collagen in the spinning thereof, and the winding speed of obtained fibers are also optional as long as they are a speed within a spinnable range.

The equipment usable for spinning the solubilized collagen solution may be a gear-pump or dispenser for general purposes, or various extruding equipment and the like, but is preferably equipment which can extrude the collagen solution in a fixed amount stably with minimum pulsation in order to provide uniform spinning.

Additionally, the diameter size of the orifice of a spinning head or needle used for spinning is not particularly limited as long as spinning is possible. An extensively large orifice is disadvantageous because it is difficult to make a membranous substance from the fibrous material because the non-woven fabric will be too bulky and an extremely narrow orifice is also disadvantageous because it is difficult to obtain sufficient membrane strength. Accordingly, the diameter of the orifice is usually in a range of 5 $\mu$m to 1 mm, preferably 50 to 700 $\mu$m. The orifice number of a spining head is one or more. Further, the shape of the orifice is also especially not limited, but a slit-like shape or other various shapes may be used as long as spinning is possible. Further, the length of the spinning head orifice is also not limited but a longer orifice is preferred in order to orient the collagen molecules in the solubilized collagen molecules as much as possible.

The coagulating bath in wet spinning is not limited if it is possible to generally coagulate collagen, and useful baths include an aqueous solution of an inorganic salt, an organic solvent containing solubilized inorganic salt therein, alcohols, ketones, and a combination of these components. Among these coagulating baths, for example, an aqueous solution of an inorganic salt includes sodium sulfate, sodium chloride, ammonium sulfate, calcium chloride, magnesium chloride, and the like, but sodium chloride, sodium sulfate or ammonium sulfate is especially suitable for spinning. These inorganic salts may be dissolved or dispersed in alcohol or acetone to make an organic solvent containing solubilized inorganic salts, which may also be utilized as the bath. In particular, a solution in which sodium chloride is dissolved or dispersed in ethanol is preferable.

Further, suitable alcohols include methanol, ethanol, isopropanol, amylalcohol, and the like, and especially, ethanol is preferable for medical use. Ketones include acetone, methylethylketone and the like.

When combined with various cross-linking agents as described below, the solution for coagulating ceases from serving simply as a coagulating bath and is useful for a cross-linking treatment as well as collagen coagulation. For example, when a mixed solution of ethanol and glutaraldehyde is used for a bath for both coagulation and cross-linking, both processes can be concurrently carried out, and cross-linking can be done by immersing the spun collagen fiber as it stands. These concurrent processes not only simplify the overall process but also are highly beneficial for spinning of dilute collagen solutions or spinning of fibers with a thin diameter.

Of the methods for forming the above non-woven fabric layer, a specific example particularly preferred is described below. A spinning head for extruding a collagen has an orifice diameter of about 200 µm and an orifice length of about 15 to 20 mm, and a solubilized collagen solution is extruded without pulsation through the spinning head by means of a dispenser or the like, and then desirably wet-spun in a 99.5 vol % ethanol coagulating bath. When the solubilized collagen is extruded into the 99.5 vol % ethanol coagulating bath, the extrusion mouthpiece is moved whenever necessary so as to extrude continuously the fibers that are spun out and cross or lay the fibers over one another in an arbitrary direction to form layers of the fibers. After the fibers are multi-layered, the coagulation solution is removed, and the fibers are washed with ethanol again and then subjected to vacuum drying to obtain excellent soft fibrous materials. This method is beneficial especially in simplification or shortening of the process and in economy because of concurrent spinning and formation of a non-woven fabric.

The above example is representative, but the invention is not limited thereto as long as the fibrous materials can be obtained. For example, the staple short fiber mentioned above may be used. It is possible to change, without causing any inconvenience, conditions such as the sort of coagulating bath, to use or not to use a mixed bath of coagulating bath and cross-linking agent, or a drying method, or to change the combination of conditions.

Preferably, the non-woven fabric layer obtained in the above method is further cross-linked in order to obtain a sufficient suture strength. This is because cross-linking improves physical strength especially under wet conditions, so that strength necessary for suturing can be sufficiently secured. Additionally, cross-linking also prolongs markedly the time the membrane takes to be discomposed and absorbed after it is implanted in a living body, as compared with the case where cross-linking is not performed.

Owing to the cross-linking treatment, the membrane can remain in a living body while maintaining a necessary membrane strength until reconstruction of an injured surface and tissue regeneration are completed after a defective part of the body is repaired, augmented or replaced, and organ or tissue malfunction due to the defect is prevented.

Cross-linking methods are roughly classified into a physical cross-linking method and a chemical cross-linking method. The physical cross-linking method includes a cross-linking by means of γ-ray, ultraviolet ray, electron beam, plasma, thermal dehydration, etc. On the other hand, a representative example of the chemical cross-linking method includes a treatment with aldehydes such as dialdehyde and polyaldehyde, epoxy compounds, carbodiimides, isocyanate compounds, tannin, chromium, etc. Of these, useful aldehydes include formaldehyde, glutaraldehyde, glyoxal, malondialdehyde, succinyl dialdehyde, phthalaldehyde, dialdehyde starch, polyacrolein, polymethacrolein, and the like, but any aldehyde can be used as long as it causes a cross-linking reaction with collagen. Epoxy compounds include glycerol-diglycidylether, sorbitol-diglycidylether, ethyleneglycol-diglycidylether, polyethyleneglycol-diglycidylether, polyglycerol-polyglycidylether and the like. Other epoxy compounds that can cause a cross-linking reaction with collagen are also usable. Though a particularly suitable example of carbodiimides is a water soluble carbodiimide, any carbodiimide can be used as long as a similar reaction is caused. Representative examples of isocyanate compounds include hexamethylene diisocyanate, tolylene diisocyanate and the like. However, useful isocyanates are not limited thereto and any isocyanate that has two or more isocyanate groups involved with a cross-linking reaction can be used, for it can perform cross-linking on collagen.

The non-woven fabric (fibrous material) obtained by spinning and so forth according to the above method may be further compressed in order to obtain a higher suture strength. The compression allows the non-woven fabric layer to increase the fiber density, producing a preferable membranous substance with more strength.

The collagen non-woven fabric can be compressed by means of a general press, but because of its intended medical use, it is preferable to compress the fabric while it is aseptically packaged with a sufficiently tough sterilized package material, for example, an aluminum package or a high-strength resinous packaging material.

On this occasion, a pressure for compressing the non-woven fabric is not limited if it does not tear down the body of the non-woven fabric layer, and usually a preferable pressure is 10 kgf/cm$^2$ to 1000 kgf/cm$^2$.

The non-woven fabric layer is preferably compressed and thinned as much as possible not only to increase the bulk density (fiber density) for the purpose of improving strength, but also from the view of handling in medical use when the non-woven fabric layer is processed into its final form of an adhesion-preventing membrane that has a layered structure. The non-woven fabric layers thus thinned are laminated to have a multi-layered structure so that an adhesive-preventing membrane with even higher suture strength can be obtained. The bulk density after compression (fiber density) is preferably 0.1 to 5 g/cm$^3$.

To improve the physical strength of the non-woven fabric layer or compressed non-woven fabric layer obtained by the above method, a binder treatment can be carried out. The binder is preferably a solubilized collagen solution. This is a method in which the non-woven fabric layer or the compressed non-woven fabric layer is immersed in a solubilized collagen solution and then dried by a suitable drying method such as natural drying, air drying, vacuum drying, or drying under low temperature so that the fibers in the non-woven fabric layer are combined with each other to make them membranous.

The physical strength of the membranous substance obtained by this binder treatment is much more improved over that of a simple non-woven fabric layer, and therefore, the suture strength is also remarkably improved. In addition, these immersion and drying processes can be repeated several tens of times or more, without any inconvenience, depending on the required physical strength.

However, unless the non-woven fabric layer or compressed non-woven fabric layer is cross-linked, the non-woven fabric layer itself may be dissolved in the solubilized collagen solution when it is immersed therein in the binder treatment. Therefore, the fabric layer is preferably cross-linked previously by the above or other methods. In addition, along with an immersion treatment, there are a method in which the solubilized collagen solution is charged in a suitable vessel or mold containing the non-woven fabric layer and a method in which the solubilized collagen solution is directly applied to the non-woven fabric layer for improving the physical strength of the fabric layer.

A sponge layer made of collagen in the present invention is a micro-porous collagen layer, and the pore diameter varies depending on the type of collagen, producing method, etc. The percentage of the pores in the sponge layer (the pore rate) is usually 10 to 90%.

In one embodiment of the present invention the membranous substance has one to six, preferably one to three layers of a collagen non-woven fabric layer. Said membranous substance has a thickness of 0.05 mm to 100 mm, preferably 0.1 mm to 50 mm, more preferably 0.2 mm to 40 mm. The surface of the membranous substance is a gelatin or hyaluronic acid layer. Preferably, one to four layers of the gelatin or hyaluronic acid are contained, and each layer is in a form of a film or sponge having a thickness of 0.05 mm to 20 mm.

Another embodiment of the present invention is a membranous substance that has a laminated structure comprising a non-woven fabric layer made of collagen fibers and a sponge layer made of collagen. In particular, the collagen non-woven fabric layer has a thickness of 0.05 mm to 100 mm, preferably 0.1 mm to 50 mm, more preferably 0.2 mm to 40 mm, the collagen sponge layer has a thickness of 0.05 mm to 20 mm, preferably 0.1 mm to 20 mm, and the present membranous substance has one to six layers of collagen non-woven fabric layer and one to four layers of collagen sponge layer. The surface of the membranous substance is a gelatin or hyaluronic acid layer. Preferably, one to four layers of the gelatin or hyaluronic acid are contained, and each layer is in a form of a film or sponge having a thickness of 0.05 mm to 20 mm, preferably 0.1 to 10 mm.

Though the non-woven fabric layer in the membranous substance in the present invention has enough membrane strength to withstand suturing by itself, the membrane strength can be further improved by a binder treatment. There are two binder treatment methods. One is such that the membranous substance is obtained by sandwiching a non-woven fabric layer between collagen layers previously dried to assure a sponge form. The membranous substance is put under normal pressure or reduced pressure in the presence of a dilute collagen solution or water to dissolve the solubilized collagen sponge layer, the dissolved layer is sufficiently absorbed into the non-woven fabric layer, and then the substance is dried by various drying methods. According to another method, the sponge layer and the non-woven fabric layer are simultaneously compressed, burying the non-woven fabric layer into the sponge layer to obtain the membranous substance. The membranous substance is also treated similarly to the above binder treatment.

In the binder treatment using this sponge layer, the time expended in drying in a later process is short because only a very small amount of a solvent component such as water is required relative to the amount of collagen that is actually used, owing to the combined fibers of the non-woven fabric layer. Further, contractive deformation or the like upon drying takes place much less frequently, which is a great merit. In a usual immersion process, a substantial amount of collagen in the solubilized collagen solution for immersion is about a few percent maximum from a practical solution viscosity, and the rest, i.e., 90% or more of the solution is a solvent component such as water. The usual immersing process is simple but unreasonable because immersion and drying operations not only take much time but also have to be repeated. Needless to say, the above are merely representative examples and are not intended to limit the invention thereto. Any method is usable as long as the fibers of the non-woven fabric layer or the compressed non-woven fabric layer are combined with each other using the solubilized collagen, to form them into a membranous substance.

In the present invention, it is optionally required that the collagen non-woven fabric layer obtained by the above method in the present invention further has the collagen sponge layer, and required that the gelatin or hyaluronic acid layer is formed on the surface of the laminated membranous substance. Following a conventional method, the gelatin or hyaluronic acid layer is readily formed by lyophilization or other method. A specific method for manufacturing the membranous substance comprises: (1) immersing the non woven fabric layer treated with the binder in a vessel filled with a collagen solution; (2) adjusting the position of the fabric layer so that it stays in the middle depth of the collagen solution; (3) freezing the vessel; (4) performing lyophilization to obtain a collagen sponge layer; (5) compressing the resultant layers to obtain the membranous substance; (6) immersing the membranous substance in a vessel filled with a hyaluronic acid solution; (7) performing freezing, lyophilization, and compression as in a hyaluronic acid sponge layer; and, finally, (8) performing thermal dehydration cross-linking on the adhesion-preventing membrane.

The processes of forming the collagen sponge layer and the gelatin or hyaluronic acid sponge layer are not limited in their order, way or the like. A method is given by way of example, which comprises producing each sponge layer separately, and then, joining them with the collagen non woven fabric layer using solubilized collagen as an adhesive.

Additionally, there is a method in which the collagen non-woven fabric layer is immersed in a solubilized collagen solution, frozen, similarly again immersed in the gelatin or hyaluronic acid solution and these are frozen to be integrated and lyophilized so as to simultaneously obtain the collagen layer and the gelatin or hyaluronic acid layer, which are layered to form the sponge laminate. However, since these methods are for maintaining the sponge layer integrated with the non-woven fabric layer without being peeled off or separated easily when the laminated product is transplanted into a living body, any method may be used if the purpose is accomplished.

As to manufacture of the sponge layer, the solubilized collagen solution, gelatin solution, hyaluronic acid solution, or other solution is poured into a vessel or charged in the vessel until a desired depth is obtained, frozen sufficiently by a general freezer and then, dried by a lyophilizer to produce a uniform sponge layer. The diameters of minute pores formed in the sponge depend upon various conditions such as the concentration of the solubilized collagen solution, gelatin solution or hyaluronic acid solution, the solvent thereof, the temperature of freezing and the freezing time.

The thickness of the respective sponge layer and total amounts of the substances used for the sponge layer can be suitably controlled in consideration of the decomposition and absorption time when the sponge is transplanted into a living body and of the effects on the guided tissue regeneration. In view of these considerations, the concentration of solubilized collagen solution is generally 0.5 to 5 wt %, and preferably, 1 to 3 wt %. The concentration range of the gelatin solution is 0.5 to 60 wt %, and preferably, 5 to 40 wt %. Further, the concentration range of the hyaluronic acid solution is preferably 0.1 to 50 wt %.

The freezing temperature is −196° C. to −10° C., and preferably, −80° C. to −10° C. This is a temperature capable of being provided by a general freezer or deep-freezer. The lyophilizer is not particularly limited as long as it is capable of stable drying.

Further, the solubilized collagen solution, gelatin solution or hyaluronic acid solution is charged in the vessel in such an amount that the thickness of the finished sponge is about 1 mm to 20 mm in general. This thickness may be changed whenever necessary according to the purposes of their usage, and is not limited to these exemplifications.

The total amount of the respective substances and the thickness of the respective sponge layers for the collagen sponge layer, gelatin sponge layer and hyaluronic acid sponge layer are desirably determined such that each sponge layer remains in a living body for about one to four weeks in general, so as not to interfere with the adhesion-preventing effect on an implanted part, repair of a damaged or cut part, or induction of tissue regeneration and the like.

Incidentally, the hyaluronic acid or gelatin layer exerting an adhesion-preventing effect is not limited to the shape of the sponge but may be manufactured as, for example, a film obtained by a usual casting method. When the gelatin or hyaluronic acid layer is formed in order to provide an adhesion-preventing effect, various modes may be selected to suit the intended purpose. For example, the gelatin or hyaluronic acid layer covers one surface or both surfaces of the membrane, or covers a part of the surface or the entire surface. The forming method of the gelatin or hyaluronic acid layer or where to form the layer is not particularly limited.

Throughout the adhesion-preventing membrane of the present invention, collagen and gelatin or hyaluronic acid, compose the membrane. Therefore, cross-linking is performed by the above various cross-linking methods on the sponge layer, the non-woven fabric layer and the gelatin or hyaluronic acid layer which compose the membrane, and on a part of or the entirety of the adhesion-preventing membrane in which these layers are laminated and integrated.

The order and the way of cross-linking can be freely combined and is not particularly limited. Most desirably, the collagen non-woven fabric layer is treated with an aldehyde such as glutaraldehyde, the collagen sponge layer and the gelatin or hyaluronic acid layer are formed and integrated with the collagen non-woven fabric layer and, lastly, thermal dehydration cross-linking is carried out. In these methods, the process of mixing coagulating agents such as ethanol with cross-linking agents represented by glutaraldehyde to simultaneously carry out spinning and cross-linking is also included.

The adhesion-preventing membrane finally obtained through the method according to the present invention is excellent in the effects of suture strength, biocompatibility, and induction of tissue regeneration.

In addition, when the binder treatment is carried out in the collagen non-woven fabric layer, it is preferable that the collagen layer formed in the binder treatment is also subjected to thermal dehydration cross-linking. This, however, is merely an example and, for example, thermal dehydration cross-linking may be performed on all of the layers without causing any inconvenience. Also, the layers may be irradiated with gamma rays for both sterilization and cross-linking. That is, the combination of cross-linking, and the order in the manufacturing process of the present adhesion-preventing membrane are not limited as long as the cross-linking can be sufficiently carried out to an extent that the above purpose of the cross-linking is established.

The adhesion-preventing membrane having the non-woven fabric layer and the respective sponge layers obtained by the above method can be further compressed. After the respective sponge layers or the non-woven fabric layers are separately compressed, they may be integrated with non-woven fabric layers or respective sponge layers which are not compressed. It is particularly preferable that the non-woven fabric layers integrated with respective sponge layers are simultaneously compressed in the final process of the production of the membrane. The compression causes a decrease in thickness of the membrane, and the compressed membrane brings about improvement in handling, for example, penetrability of a suturing needle during suturing and desired-shape cutting when the adhesion-preventing membrane is used in a surgical operation or the like. Therefore, transplant surgery and others can be carried out smoothly. The compression can be carried out by a general compressor in the same manner as the compression of the non-woven fabric layer. However, it is desirable that the compression is made while the membrane is aseptically wrapped with a sufficiently tough sterilized packaging material such as an aluminum package or a high-strength resinous packaging material, because of the intended medical use. Further, the pressure when compressing the adhesion-preventing membrane is not limited if it is within a range that does not destroy the membrane itself, and a normally preferred pressure is 10 to 1000 $kgf/cm^2$.

EXAMPLES

The following examples are given to further illustrate in detail the present invention.

Example 1

First, in an Erlenmeyer flask (Corning Company), while chicken-derived atelo-collagen was gently stirred with a magnetic stirrer, distilled water for injection, i.e., water suitable for injection according to Japanese Pharmacopoeia, was added thereto to prepare two kinds of collagen solutions having concentrations of 3 wt % and 5 wt %, respectively. The procedure was carried out aseptically in a clean bench.

Then, 40 ml of a 5 wt % collagen solution was continuously extruded into a 99.5 vol % ethanol solution (Wako Pure Chemical Industry Co., Ltd., special grade), as a coagulation bath, under a constant pressure condition of 4.0 bar using a dispenser (manufactured by Scientific Co.: EFD 900 type) equipped with a syringe and 27 gauge needle (orifice diameter=200 μm) to conduct spinning.

In the continuous extrusion spinning, the needle tip was allowed to move over the surface of the ethanol coagulation bath in a random manner so that spinning was carried out such that the settled and coagulated collagen filament crossed over itself in multiple folds to obtain a non-woven fabric (a mass of fibrous collagen). Then the non-woven fabric (mass) was left to stand for 1 hour to allow sufficient coagulation. Thereafter, in the 99.5% ethanol solution, the coagulation solution was exchanged twice to effect washing.

The above non-woven fabric (a mass of fibrous collagen) was dried as it was in a vacuum dry oven (manufactured by EYELA CO.: VOS-300VD type) for 4 hours at room temperature under reduced pressure (below 1 Torr) using an oil rotary vacuum pump (manufactured by ULVAC CO.: GCD135-XA type) to obtain the non-woven fabric (fibrous collagen non-woven fabric). The diameter of the fiber was 60 μm and the bulk density of the non-woven fabric was $4.0 \times 10^{-2}$ $g/cm^3$.

Then, the non-woven fabric was charged in a sterilized aluminum wrapping material and compressed at a pressure of 100 $kgf/cm^2$ using a High Pressure Jack (manufactured by Iuchi Seieido: 15 t press machine) to obtain compressed non-woven fabric of about 8 cm×5 cm having fibers having a diameter of 60 μm, a thickness of 0.6 mm and a bulk density of 0.9 $g/cm^3$.

Then, the compressed non-woven fabric was immersed for 4 hours in a 5% glutaraldehyde solution (manufactured by Wako Pure Chemical Industry Co., Ltd.: 25% first-grade glutaraldehyde solution diluted with distilled water for injection) to carry out a cross-linking treatment. After completion of the cross-linking reaction, the non-woven fabric was washed sufficiently with distilled water for injection and then immersed in a bath of distilled water for injection for 1 hour, followed by three exchanges of water during the dipping to remove excess glutaraldehyde. The non-woven fabric after completion of the cross-linking treatment was dried again, and compressed at a pressure of 100 kgf/cm$^2$ using a High Pressure Jack (manufactured by Iuchi Seieido: 15 t press machine) to obtain a compressed non-woven fabric of about 8 cm×5 cm which has fibers having a fiber diameter of 60 $\mu$m, a thickness of 0.6 mm, and a bulk density of the non-woven fabric of 0.91 g/cm$^3$.

Separately, a lyophilized collagen sponge was prepared for binder treatment by the following method.

First, a 3 wt % solubilized collagen solution was charged in a square container made of polystyrene to fill it to a depth of about 17 mm and then subjected to a freezing treatment at −20° C. for 12 hours in a freezer (manufactured by SANYO CO.: MEDICAL FREEZER). Then, the above frozen solubilized collagen as contained in the above container was transferred into a lyophilizer (manufactured by EYELA Co.: FDU-830 type), and lyophilized for about 24 hours under a reduced pressure (below 0.05 Torr) using an oil rotary vacuum pump (manufactured by ULVAC CO.: GCD200-XA type) to obtain a collagen sponge. After completion of the lyophilization, the sponge had a film thickness of about 15 mm and a porosity of about 80%.

One sheet of the above compressed non-woven fabric (thickness of 0.6 mm) that had been subjected to the cross-linking treatment together with one sheet of the above collagen sponge (thickness of 15 mm) that had been separately prepared were compressed again at a pressure of 100 kgf/cm$^2$ to obtain a collagen membranous substance having a size of about 7 cm×4.5 cm and a thickness of 1 mm having a two-layer structure in which the non-woven layer was embedded in the sponge layer.

Then, the above membranous substance was immersed in 15 ml of an aqueous 3 wt % solubilized collagen solution and in this state was introduced in a vacuum drying oven (manufactured by EYELA Co.: VOS-300VD type) where the pressure was reduced to remove the air in the membranous substance to forcibly impregnate the solubilized collagen solution into the sponge layer of the above membranous substance. The sponge layer in the collagen membranous substance was dissolved in water derived from the aqueous solubilized collagen solution so as to form a one layer membranous substance.

The membranous substance obtained was dried at a low temperature (4° C.) for 24 hours to obtain a collagen membranous substance treated with the binder and having thickness of 0.18 mm, and a size of about 7 cm×4.5 cm.

The obtained collagen membranous substance was transferred to a square polystyrene container and a 30 wt % gelatin solution was poured onto the membranous substance and the position of the membranous substance adjusted with a sterile pincette, so that the membranous substance was substantially positioned intermediately, and frozen at −20° C. for about 12 hours in a freezer (manufactured by SANYO CO.: MEDICAL FREEZER). A membrane in a lyophilized state having a three-layer laminated structure of gelatin layer/compressed non-woven fabric layer/gelatin layer was obtained.

This membrane having a three-layer laminated structure was lyophilized in the container at −20° C. for 24 hours similarly to the above freezing method. Then the membrane having a compressed collagen non-woven fabric layer combined with gelatin sponge layers was compressed again under a pressure of 400 kgf/cm$^3$ to obtain a membrane of a three-layer laminated structure having a thickness of about 1.6 mm (compressed non-woven fabric, 0.18 mm thick, and gelatin coatings, each 0.71 mm thick) and a size of about 7 cm×5 cm.

Then, the obtained membrane was subjected to a heat dehydration cross-linking treatment at 135° C. under reduced pressure (below 1 Torr) for 12 hours using a vacuum drying oven and an oil rotary vacuum pump (manufactured by ULVAC CO.: GCD135-XA type). Thus, an adhesion preventing membrane was obtained in which only the fibers in the collagen non-woven fabric layer were subjected to the glutaraldehyde cross-linking treatment and the respective surfaces each have a gelatin sponge layer having a thickness of 0.4 mm. The suture strength, biocompatibility, tissue regeneration induction and adhesion prevention properties of the obtained adhesion preventing membrane are shown in Examples 3 and 4 below.

FIG. 1 is a flow chart illustrating the steps in this example.

Example 2

In the same manner as in Example 1, chicken-derived atelo-collagen was dissolved into distilled water for injection to prepare a 5 wt % collagen solution. The procedure was carried out aseptically in a clean bench.

The 5 wt % collagen solution was continuously extruded in the same manner as in Example 1 into a mixed spinning bath containing 1000 ml of 99.5 vol % ethanol (manufactured by Wako Chemicals, special grade) and 42 ml of 25% glutaraldehyde under the condition of a constant pressure of 2.0 barr using a dispenser (manufactured by Scientific Co.: EFD900 type) equipped with a 20 gauge needle tip (orifice diameter 600 $\mu$m). A non-woven fabric made of fibers having a diameter of 200 $\mu$m and having a bulk density of 0.01 g/cm$^3$ was obtained.

Then, the above non-woven fabric was reacted with glutaraldehyde in a coagulation and cross-linking bath containing a mixture of about 1% glutaraldehyde and ethanol for 4 hours in the same manner as in Example 1. Then, the mixed solution containing glutaraldehyde and ethanol was removed from the bath, and the non-woven fabric was washed three times with a 99.5% ethanol solution to remove the residual glutaraldehyde.

This collagen non-woven fabric was dried under reduced pressure in the same manner as in Example 1, and compressed at a pressure of 100 kgf/cm$^2$ to obtain a compressed non-woven fabric having a thickness of 0.7 mm and a size of about 7 cm×5 cm (the fiber diameter was 200 $\mu$m and the bulk density of the non-woven fabric was 0.8 g/cm$^3$). Two sheets of the obtained compressed non-woven fabric were overlaid to form a laminated structure.

Then, two sheets of the compressed non-woven fabric were charged in a square polystyrene container and a 20 wt % hyaluronic acid solution was filled into the container from the top, frozen at −20° C. for 12 hours in a freezer (manufactured by SANYO CO.: MEDICAL FREEZER) and then lyophilized for about 24 hours. Thus, a membranous substance of a 4-layer structure having the collagen non-woven fabric layers between hyaluronic acid sponge layers was obtained.

The thus-obtained membranous substance was compressed at a pressure of 500 kgf/cm$^2$ to obtain an adhesion preventing layer having a thickness of about 1.9 mm and a size of about 7 cm×5 cm. Then, the obtained membrane was subjected to a heat dehydration cross-linking treatment at 135° C. under reduced pressure (below 1 Torr) for 12 hours using a vacuum drying oven and an oil rotary vacuum pump (manufactured by ULVAC CO.: GCD135-XA type). Thus, a 4-layer structure of an adhesion preventing membrane (having a thickness of about 1.9 mm and a size of about 7 cm×5 cm) was obtained in which two laminated layers of non-woven fabric (each layer having a 0.7 mm thickness) were cross-linked with glutaraldehyde and both surfaces of the laminated layers were combined with a hyaluronic acid sponge layer having a thickness of about 0.25 mm and heat cross-linked. The suture strength, biocompatibility, induction of tissue regeneration and adhesion-preventing properties of the obtained adhesion preventing membrane are shown in Examples 3 and 4 below.

Figure 2:
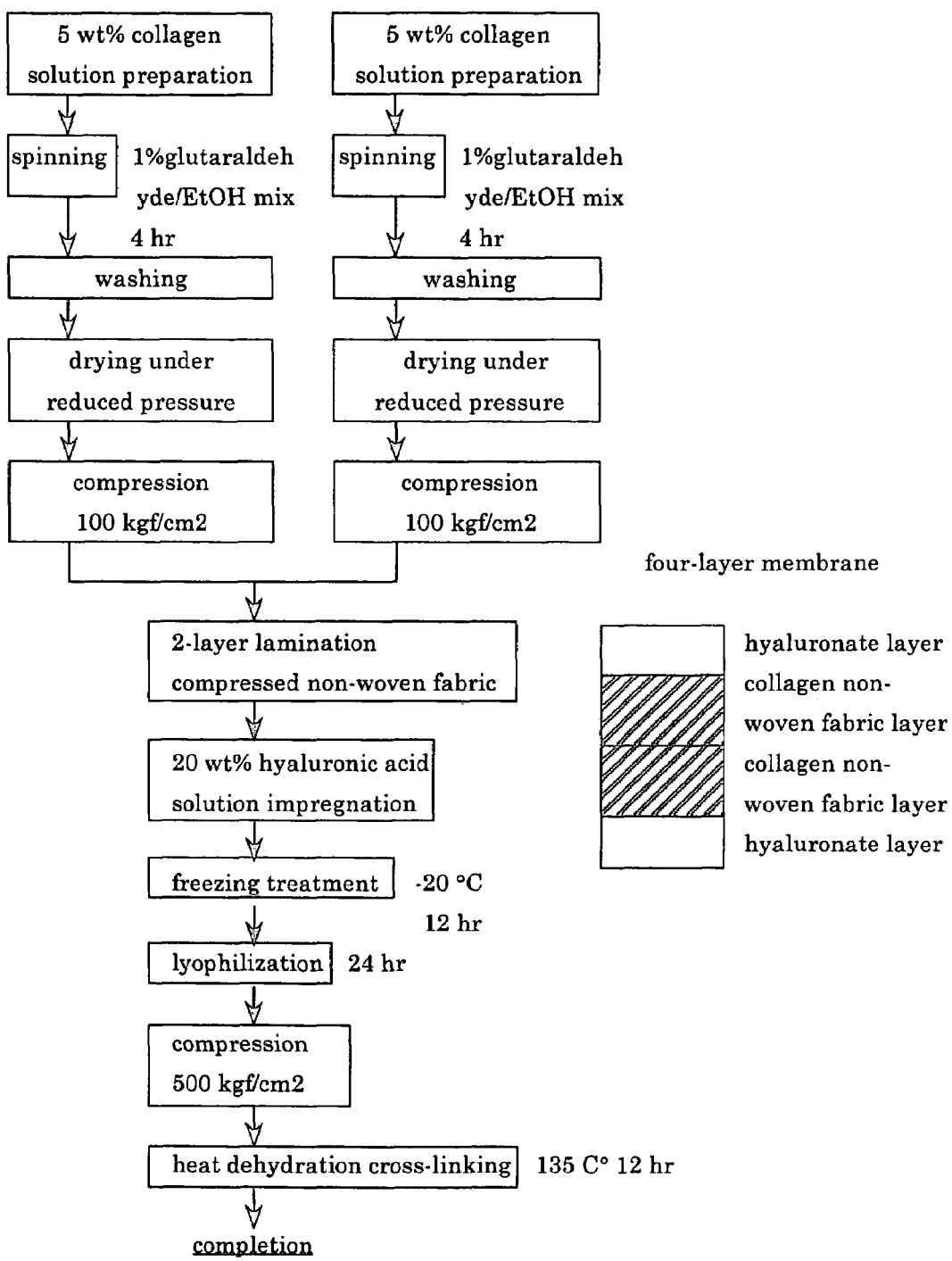

FIG. 2 is a flow chart illustrating the steps in this example.

Example 3

Measurement of Suture Strength

The suture strength of the adhesion preventing membranes prepared in Examples 1 and 2 were measured. As control samples, Goretex pericardium (manufactured by Goretex Co.: Goretex EPTFE Patch II (sheet for pericardium)), porcine extracted pericardium, and porcine extracted cerebral dura mater were used. The porcine extracted pericardium and extracted cerebral dura mater were extracted from an about 20 kg pig by an extraction operation under anesthesia and then, after extraction of each membrane, immersed in physiological saline and immediately measured in a fresh state.

The measurement method was as follows. First, sample membranes and control membranes were all cut out as plate-like sections of 1 cm×2.5 cm and in a central part of each membrane at a distance of 5 mm from an end in the direction of a longer side a suture (4-0 proline thread, manufactured by ETHICON, INC.) was passed and bound to form a ring. The section to which a suture was bound was immersed in physiological saline for 30 minutes and then taken out quickly, followed by measuring its tensile strength using a tensile strength meter (Autograph S-500D, manufactured by Shimadzu Seisakusho Co., Ltd.). The measurement was carried out under conditions where the end opposite to the end in which the suture was passed was fixed to a distance of about 10 mm from the end, and the ring-like suture at one end was engaged with a hook for measurement, which was pulled at a constant speed of 10 mm/minute to carry out the measurement. In this case, a change in strength until the section was cut by the 4-0 praline thread or the proline thread departed from the section was measured. Among the recorded strength values, the highest value was defined as a suture strength (N: Newton) of the adhesion preventing membrane.

The results are shown in Table 1.

TABLE 1

|  | Goretex pericardium | Porcine pericardium | Porcine cerebral dura mater | Example 1 | Example 2 |
|---|---|---|---|---|---|
| Measured value (N) | 8.5 | 4.0 | 8.3 | 8.5 | 5.1 |

As can be seen from Table 1, the adhesion preventing membrane of the present invention has suture strength enough to endure the usual suturing fixation.

Example 4

Implant Test

The adhesion preventing membrane obtained in Example 1 was implanted in the back muscle of rabbits (n=8) and tissue reaction was observed with the naked eye and using an optical microscope to evaluate its biocompatibility.

The implanted sample used was obtained by cutting the adhesion preventing membrane obtained in Example 1 to a size of 1.5 mm×10 mm. As a control, a high density polyethylene plate was used cut to the same size as the sample. The control was subjected to ethylene oxide gas sterilization before use. The sample membrane was used for the implanting test after sterilization by irradiation with 25 kGy γ rays.

For implanting, first, a rabbit (body weight about 2.5 kg to 3.0 kg) was subjected to ordinary inhalation anesthesia and then the control and the sample were implanted aseptically so that they sandwiched the back spine of the rabbit such that the control was on the left hand side and the sample was on the right hand side of the back spine of the rabbit. The implanting method was such that a sterilized 15 gauge syringe punctured obliquely the surface of skin at an angle of about 30 degrees, and the sample membrane and control were pushed out, thus implanting them in the muscle of rabbit. After this, four rabbits were used after 1 week and another four rabbits were used after 4 weeks from the implanting as objects of observation.

At each observation time, only two out of the four rabbits were incised at the implanted part under anesthesia and observation of the implanted portion and peripheral tissues was made visually centered on an inflammatory reaction, etc. The remaining two rabbits were sacrificed with excessive anesthesia and after the peripheral tissue containing the implanted portion was extracted, ordinary formalin fixation was conducted and then a section was prepared, which was observed under a microscope.

From the results of these observations, the sample membrane showed no significant inflammatory reaction, etc. as compared with the control at any observation time for all rabbits, thus revealing that the adhesion-preventing membrane obtained by the present invention has good biocompatibility. In the case where 4 weeks elapsed from the implanting, it was observed that the sample membrane was decomposed and absorbed.

Example 5

Study of Adhesion Preventing Effect

Ten rats (body weight 250 g to 300 g) were divided into two groups each consisting of 5 rats, one group being a control and the other a sample group which used the adhesion preventing membrane prepared in Example 1. For each of the control group and sample group, the rats were narcotized intramuscularly and thereafter the narcotized state was retained by inhalation anesthesia. For the control group, the rats were incised at the abdomen under anesthesia to expose the cecum and then the chorion of a size of about 5 mm square was peeled off. The abdominal portion corresponding to the cecum chorion was peeled off similarly and an adhesion model in which the injured surface of the cecum and the injured abdominal surface served as connection surfaces was prepared. Thereafter, for the control group, the abdomen was stitched without any further treatment.

On the other hand, for the sample group, an adhesion model was prepared in the same manner as the control group and thereafter the injured cecum surface was covered with the adhesion preventing membrane prepared in Example 1 and fixed. The size of the fixed adhesion preventing membrane was on the order of about 10 mm×10 mm and the membrane was sutured and fixed at the four corners thereof being lightly hung on the intestinal tract with a suture (5-0 bicryl thread). For both the sample group and the control group, the rats were reoperated after two weeks for celiotomy to visually observe the respective states of adhesion.

The degree of adhesion upon visual observation was judged based on the criteria in Table 2 below and assigned score to comparatively evaluate the sample group and control group. Rank 3 or higher was adopted for concluding that adhesion occurred.

TABLE 2

| | State/Condition | Score | Rank |
|---|---|---|---|
| Degree of adhesion | No adhesion | 0 | 1 |
| | Membranous adhesion (readily manually peelable) | 1 | 2 |
| | Fibrous adhesion (readily peelable by incision, etc.) | 2 | 3 |
| | Restiform adhesion (Peeling by incision is needed) | 3 | 4 |
| | Membranous adhesion (Difficult to peel without giving injury to the tissue) | 4 | 5 |

TABLE 3

| | Control group | Sample group |
|---|---|---|
| Average score | 3.2 | 0.6 |
| Number of adhesion confirmed | 5 cases | 0 case |

As a result of the comparative study between the sample group and the control group based on the criteria in Table 3, there was in the sample group no case in which adhesion was observed while in the control group adhesion at Rank 3 or higher was observed for all cases. In the sample group, the adhesion preventing membrane remained at the fixed part but did not move to other parts for almost all of the cases so that it served to separate the injured surfaces from each other. Further, the remained adhesion preventing membrane was carefully peeled off and the injured surface of the cecum was visually observed. As a result, it was observed that the injured surface started to heal.

Example 6

First, in an Erlenmeyer flask, while chicken-derived atelocollagen was gently stirred with a magnetic stirrer, distilled water for injection was added thereto to prepare two kinds of collagen solutions having concentrations of 3 wt % and 5 wt %, respectively. The procedure was carried out aseptically in a clean bench.

Then, 40 ml of a 5 wt % collagen solution was continuously extruded into a 99.5 vol % ethanol liquid (Wako Pure Chemical Industry Co., Ltd., special grade), which is a coagulation bath, under a constant pressure condition of 4.0 bar using a dispenser (manufactured by Scientific Co.: EFD 900 type) equipped with a syringe and a 27 gauge needle to conduct spinning.

In the continuous extrusion spinning, the needle tip was allowed to move over the surface of the ethanol coagulation bath in a random manner so that spinning was carried out such that the settled and coagulated collagen filament crossed over in multiple folds to obtain a non-woven fabric (a mass of fibrous collagen). Then the non-woven fabric (mass) was left to stand for 1 hour to allow sufficient coagulation. Thereafter, in the 99.5% ethanol solution, the coagulation solution was exchanged twice to effect washing. The diameter of the fiber was 60 µm and the bulk density of the non-woven fabric was 0.9 g/cm$^3$.

The above non-woven fabric (a mass of fibrous collagen) was dried as it was in a vacuum drying oven (manufactured by EYELA CO.: VOS-300VD type) for 4 hours at room temperature —under reduced pressure (below 1 Torr) using an oil rotary vacuum pump (manufactured by ULVAC CO.: GCD135-XA type) to obtain a non-woven fabric (fibrous collagen non-woven fabric). Then, the non-woven fabric was charged in a sterilized aluminum wrapping material and compressed at a pressure of 100 kgf/cm$^2$ using a High Pressure Jack (manufactured by Iuchi Seieido: 15 t press machine) to obtain a compressed non-woven fabric of about 8 cm×5 cm (the diameter of fibers was 60 µm, the bulk density of non-woven fabric was 0.9 g/cm$^3$).

Then, the compressed non-woven fabric was immersed for 4 hours in a 5% glutaraldehyde solution (manufactured by Wako Pure Chemical Industry Co., Ltd.: 25% first-grade glutaraldehyde solution diluted with distilled water for injection) to carry out a cross-linking treatment. After completion of the cross-linking reaction, the non-woven fabric was washed sufficiently with distilled water for injection and then immersed in a bath of distilled water for injection for 1 hour, followed by three exchanges of water during the dipping to remove excess glutaraldehyde. The non-woven fabric after completion of the cross-linking treatment was dried, charged in a sterilized aluminum wrapping material, and compressed at a pressure of 100 kgf/cm$^2$ using a High Pressure Jack (manufactured by Iuchi Seieido: 15 t press machine) to obtain a compressed non-woven fabric of about 8 cm×5 cm (the diameter of fibers was 60 µm, the bulk density of the non-woven fabric was 0.9 g/cm$^3$).

Separately, a lyophilized collagen sponge was prepared by the following method.

First, a 3 wt % solubilized collagen solution was charged in a square polystyrene container to fill it to a depth of about 17 mm and then subjected to a freezing treatment at –20° C. for 12 hours in a freezer (manufactured by SANYO CO.: MEDICAL FREEZER).

Then, the above frozen solubilized collagen as contained in the above container was transferred into a lyophilizer (manufactured by EYELA Co.: FDU-830 type), and lyophilized for about 24 hours under a reduced pressure (below 0.05 Torr) using an oil rotary vacuum pump (manufactured by ULVAC CO.: GCD200-XA type) to obtain a collagen sponge. After completion of the lyophilization the sponge had a film thickness of about 15 mm and a porosity of about 70%.

One sheet of the above compressed non-woven fabric (0.6 mm thick) that had been subjected to the cross-linking treatment together with two sheets of the above collagen sponge (15 mm thick) that had been separately prepared was compressed again at a pressure of 100 kgf/cm$^2$ to obtain a collagen membranous substance having a size of about 8 cm×5 cm having a three-layer structure in which the non-woven layer was embedded in the sponge layers. The surface layers of the (sponge layer/non-woven layer/sponge layer) are collagen sponge layers.

Then, the above membranous substance was immersed in 15 ml of an aqueous 3 wt % solubilized collagen solution and in this state was introduced in a vacuum drying oven (manufactured by EYELA Co.: VOS-300VD type) where the pressure was reduced to remove the air in the membranous substance to forcibly impregnate the solubilized collagen solution into the sponge layers of the above membranous substance. The obtained membranous substance of which the sponge layers were dissolved was dried at a low temperature (4° C.) for 24 hours.

The dry membranous substance was transferred to a square polystyrene container and a 3 wt % solubilized collagen solution was poured onto the dry membranous substance to a depth of 15 mm. After adjustment of the position of the membranous substance with a sterile pincette, etc. so that the membranous substance was substantially positioned intermediately in the solution, it was frozen at −20° C. for about 12 hours in a freezer (manufactured by SANYO CO.: MEDICAL FREEZER). Further, lyophilization was conducted to obtain a membrane in a lyophilized state having a three-layer laminated structure of collagen sponge layer/non-woven fabric layer/collagen sponge layer.

The above collagen membranous substance in a lyophilized state was compressed at a pressure of 200 kgf/cm$^2$ and then immersed in a 30 wt % gelatin solution. Similarly, a freezing treatment was conducted at −20° C. for 12 hours. Thus, a membrane in a lyophilized state having a 5-layer laminated structure of gelatin layer/collagen sponge layer/collagen non-woven fabric layer/collagen sponge layer/gelatin layer was obtained.

Then, the obtained collagen membranous substance in which the compressed non-woven fabric layer and various sponge layers were integrated was compressed again similarly at a pressure of 400 kgf/cm$^2$ to obtain a collagen membranous substance of a 5-layer structure (gelatin layer/collagen sponge layer/collagen non-woven fabric layer/collagen sponge layer/gelatin layer) having a thickness of about 1.6 mm and a size of about 8 cm×5 cm. The total thickness of collagen sponge layers and non-woven fabric layers is 1.0 mm and the thickness of each gelatin layer is 0.3 mm.

Then, the obtained membrane was subjected to a heat dehydration cross-linking treatment at 1350° C. under reduced pressure (below 1 Torr) for 12 hours using a vacuum drying oven and an oil rotary vacuum pump (manufactured by ULVAC CO.: GCD135-XA type). Thus, an adhesion preventing membrane was obtained in which only the fibers in the collagen non-woven layer were subjected to the glutaraldehyde cross-linking treatment and the heat dehydration cross-linking. The suture strength, biocompatibility, tissue regeneration induction and adhesion prevention properties of the obtained adhesion preventing membrane are shown in Examples 8 to 10 below.

Figure 3:
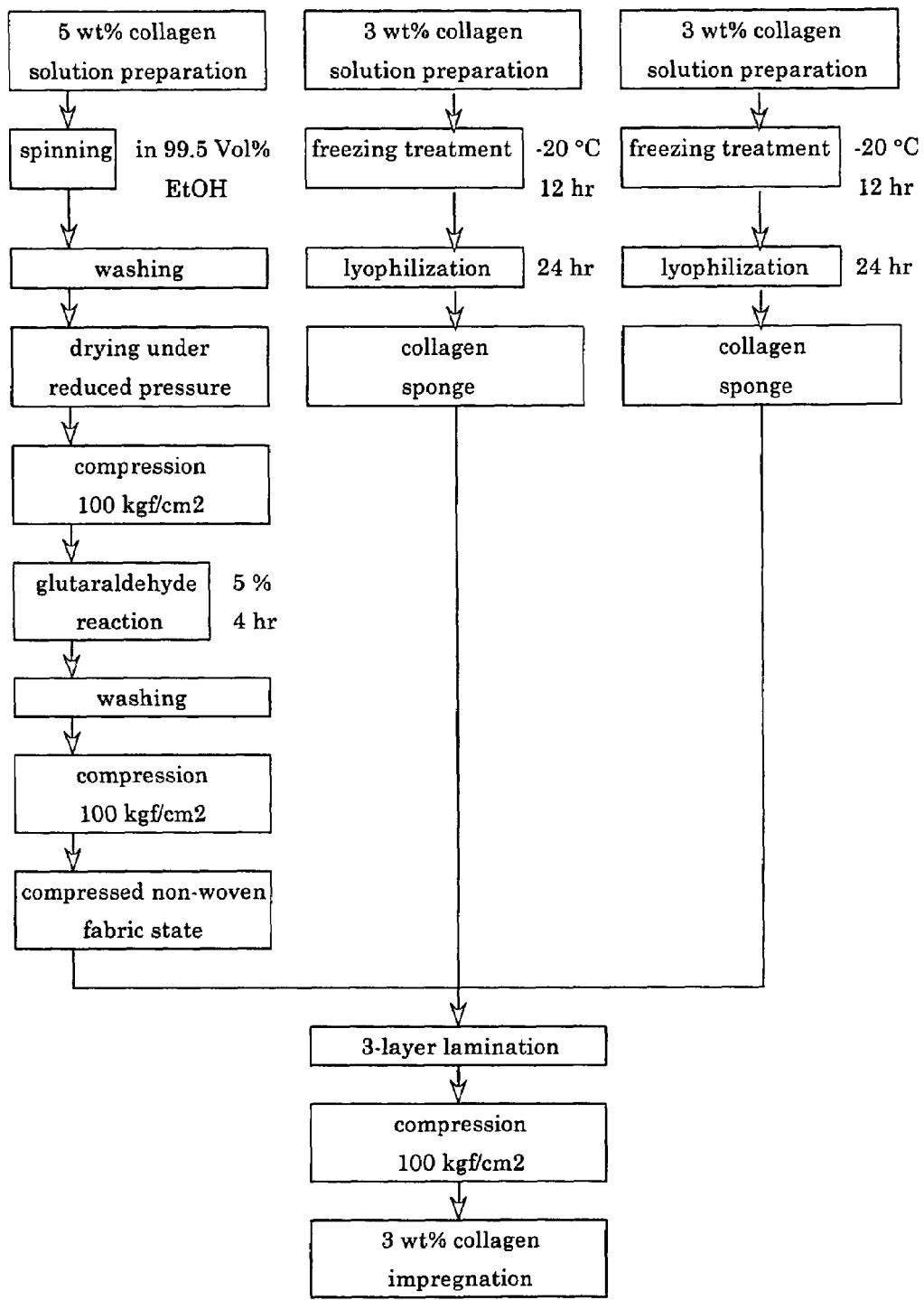
Figure 3:
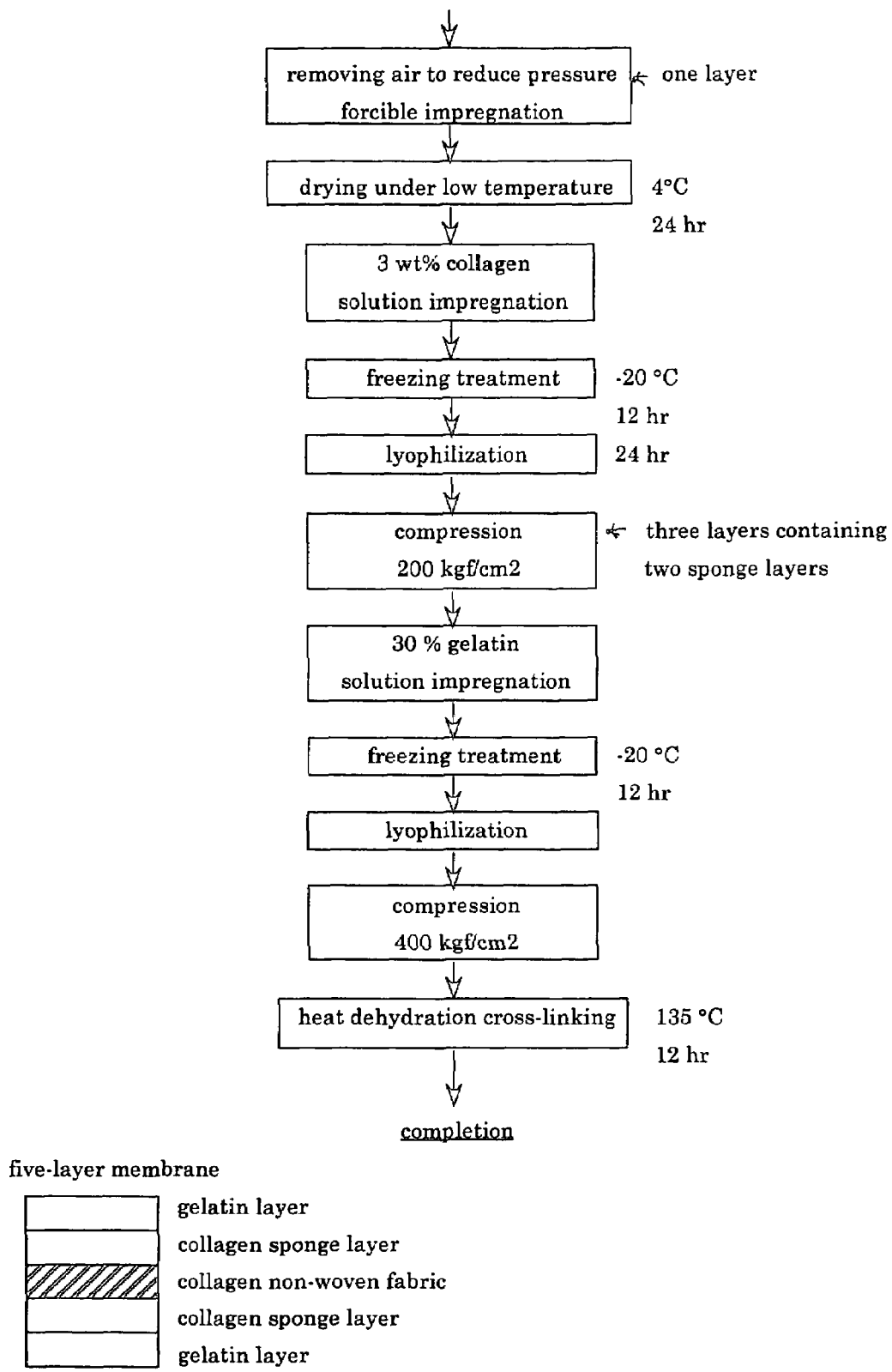

FIG. 3 is a flow chart illustrating the steps in this example.

Example 7

Non-woven fabric was obtained in the same manner as in Example 6 except that spinning was conducted under the condition of a constant pressure of 2.0 bar using a dispenser (manufactured by Scientific Co.: EFD900 type) equipped with a 20 gauge needle (orifice diameter 600 µm). Then, the obtained non-woven fabric was subjected to glutaraldehyde treatment in the same manner as in Example 6 for 4 hours and compressed again.

Two sheets of the obtained compressed non-woven fabric were overlaid to form a laminated structure. Then, two sheets of the compressed non-woven fabric were charged in a square polystyrene container and a 3 wt % collagen solution was filled to a depth of 15 mm, freezing was conducted at −20° C. for 12 hours in a freezer (manufactured by SANYO CO.: MEDICAL FREEZER) and then lyophilization was conducted for about 24 hours.

The obtained collagen sponge membrane containing the non-woven fabric was again impregnated with about 20 ml of a 3 wt % collagen solution to render the collagen sponge layer completely gel-like and was then dried for about 12 hours in a clean bench under ventilation. Thus, a plate-like collagen membrane was obtained in which the non-woven fabric had been subjected to binder treatment with a collagen solution.

The plate-like collagen membrane was immersed for 4 hours in a 5% glutaraldehyde solution (manufactured by Wako Pure Chemical Industry Co., Ltd.: 25% first-grade glutaraldehyde solution diluted with distilled water for injection) to carry out cross-linking. After completion of the reaction, the plate-like collagen membrane was washed sufficiently with distilled water for injection and then immersed in a bath of distilled water for injection for 2 hours, followed five exchanges of water during the dipping to remove excess glutaraldehyde.

The membranous substance after completion of the washing was dried at 4° C. for 24 hours and then transferred to a square polystyrene container and a 3 wt % solubilized collagen solution was poured onto the dry membranous substance to a depth of 15 mm. After adjustment of the position of the membranous substance with a sterile pincette, etc. so that the membranous substance was substantially positioned intermediately in the solution, it was frozen at −20° C. for about 12 hours in a freezer. The lyophilized collagen membrane together with the square polystyrene container was subjected to lyophilization for about 24 hours.

Then, the obtained collagen membranous substance in which the compressed non-woven fabric layers and sponge layers were integrated was compressed again at a pressure of 400 kgf/cm$^2$ to obtain a collagen membranous substance of a 4-layer structure having a thickness of about 1.7 mm and a size of about 8 cm×5 cm.

The membranous substance was transferred to a square polystyrene container and a 3 wt % hyaluronic acid solution was filled therein to a depth of about 10 mm and freezing/lyophilization was carried out to obtain a membranous substance having a sponge layer of hyaluronic acid.

Thus, a sponge layer of hyaluronic acid was formed on the entirety of the outer surfaces of the collagen sponge layer. The thus-obtained laminated membrane was compressed again at a pressure of 400 kgf/cm$^2$ to obtain an adhesion preventing layer of a 6-layer structure having a thickness of about 1.9 mm and a size of about 8 cm×5 cm. The total thickness of the non-woven fabric layers and sponge layers was 1.7 mm and the thickness of each hyaluronic acid layer was 0.1 mm.

Then, the obtained membrane was subjected to heat dehydration cross-linking treatment at 1350° C. under reduced pressure (below 1 Torr) for 12 hours using a vacuum drying oven and an oil rotary vacuum pump (manufactured by ULVAC CO.: GCD135-XA type). Thus, an adhesion preventing membrane was obtained in which the non-woven fabric layer and binder layer had been subjected to the glutaraldehyde cross-linking treatment and the collagen sponge layer and hyaluronic acid sponge layer had been subjected to the heat dehydration cross-linking. The suture strength of the obtained adhesion preventing membrane is shown in Example 8 below.

Figure 4:
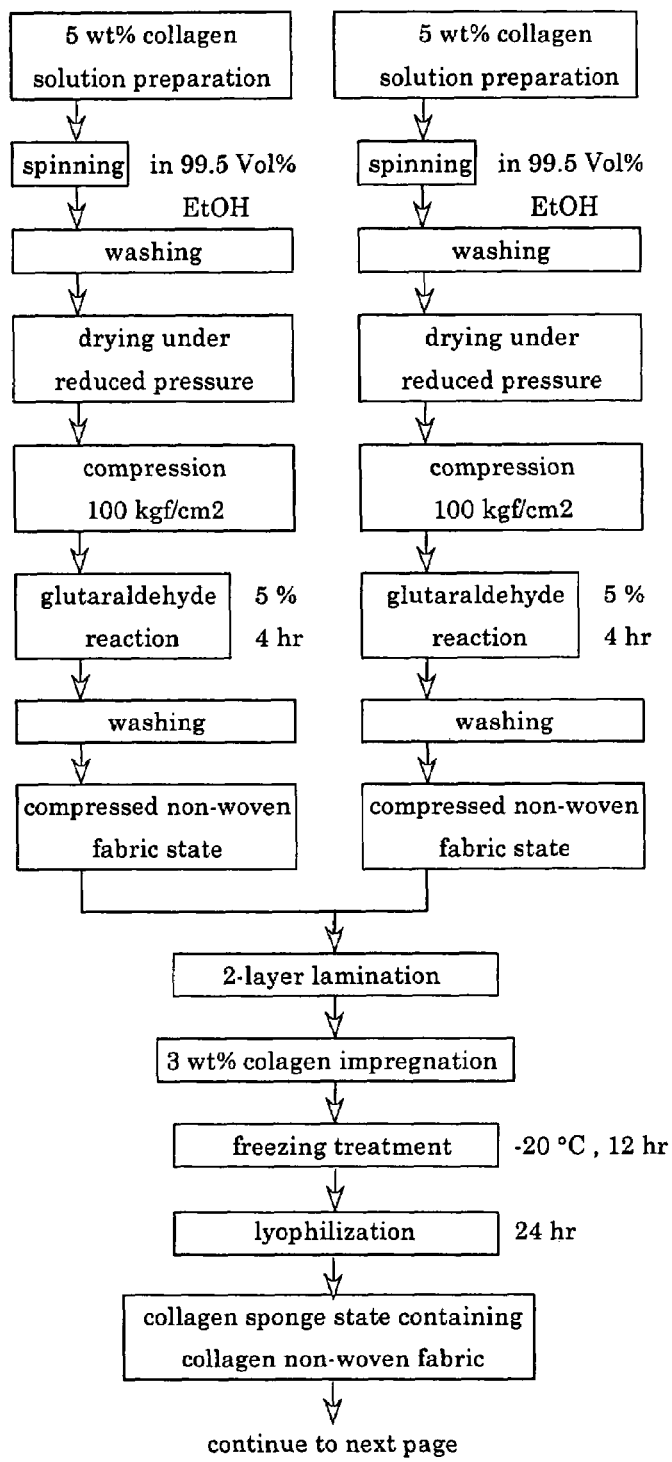
Figure 4:
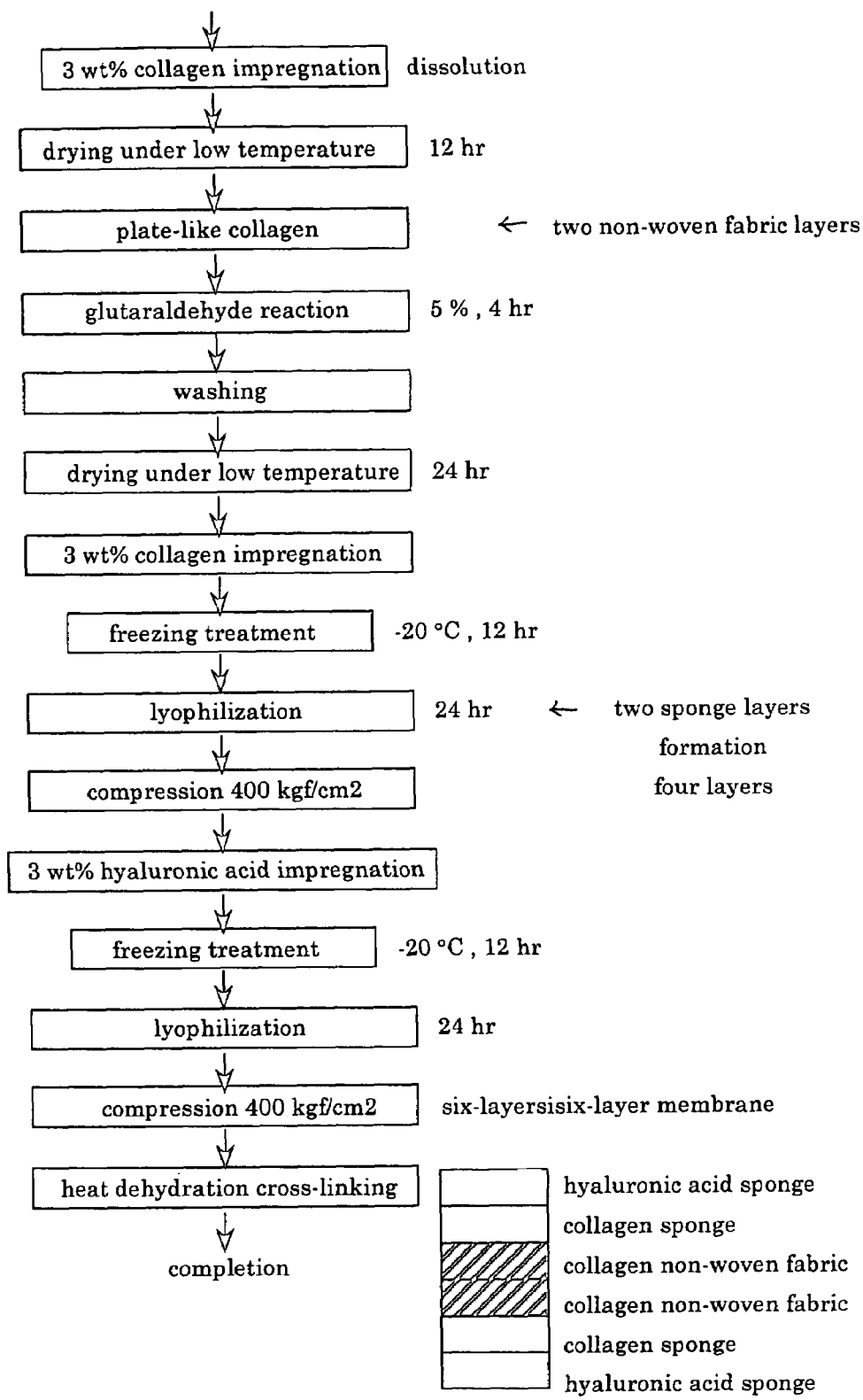

FIG. 4 is a flow chart illustrating the steps in this example.

Example 8

Measurement of Suture Strength

The suture strength of the adhesion preventing membranes prepared in Examples 6 and 7 were measured. As control samples Goretex pericardium (manufactured by Goretex Co.: Goretex EPTFE Patch II (sheet for pericardium)), porcine extracted pericardium, and porcine extracted cerebral dura mater were used. The porcine extracted pericardium and extracted cerebral dura mater were extracted from an about 20 kg pig by an extraction operation under anesthesia and then, after extraction of each membrane, immersed in physiological saline and immediately measured in a fresh state.

The measurement method was as follows. First, sample membranes and control membranes were all cut out as plate-like sections of 1 cm×2.5 cm and in a central part of each membrane at a distance of 5 mm from an end in the direction of a longer side a suture (4-0 proline thread, manufactured by ETHICON, INC.) was passed and bound to form a ring. The section to which a suture was bound was immersed in physiological saline for 30 minutes and then taken out quickly, followed by measuring its tensile strength using a tensile strength meter (Autograph S-500D, manufactured by Shimadzu Seisakusho Co., Ltd.). The measurement was carried out under conditions where the end opposite to the end in which the suture was passed was fixed to a distance of about 10 mm from the end, and the ring-like suture at one end was engaged with a hook for measurement, which was pulled at a constant speed of 10 mm/minute to carry out the measurement. In this case, a change in strength until the section was cut by the 4-0 proline thread or the proline thread departed from the section was measured. Among the recorded strength values, the highest value was defined as a suture strength (N: Newton) of the adhesion preventing membrane of the present invention.

The results are shown in Table 4.

TABLE 4

|  | Goretex pericardium | Porcine pericardium | Porcine cerebral dura mater | Example 6 | Example 7 |
| --- | --- | --- | --- | --- | --- |
| Measured value (N) | 8.5 | 4.0 | 8.3 | 8.5 | 8.8 |

As can be seen from Table 4, the adhesion preventing membrane of the present invention is equivalent to Goretex pericardium (manufactured by Goretex Co.: Goretex EPTFE Patch II (sheet for pericardium)) in suture strength, and superior to porcine extracted pericardium and porcine cerebral dura mater.

Example 9

Implant Test

The adhesion preventing membrane obtained in Example 6 was implanted in the back muscle of rabbits (n=8) and tissue reaction was observed with naked eyes and using an optical microscope to evaluate its biocompatibility.

The implanted sample used was obtained by cutting the adhesion preventing membrane obtained in Example 6 to a size of 1.5 mm×10 mm. As a control a high density polyethylene plate was used cut to the same size as the sample. The control was subjected to ethylene oxide gas sterilization before use. The sample membrane was used for the implanting test after sterilization by irradiation with 25 kGy γ rays.

For implanting, first a rabbit (body weight about 2.5 kg to 3.0 kg) was subjected to ordinary inhalation anesthesia and then the control and the sample were implanted aseptically so that they sandwiched the back spine of the rabbit such that the control was on the left hand side and the sample was on the right hand side of the back spine of the rabbit. The implanting method was such that a sterilized 15 gauge syringe punctured obliquely the surface of skin at an angle of about 30 degrees, and the sample membrane and control were pushed out, thus implanting them in the muscle of rabbit. After this, four rabbits were used after 1 week and another four rabbits were used after 4 weeks from the implanting as objects of observation.

At each observation time, only two out of the four rabbits were incised at the implanted part under anesthesia and observation of the implanted portion and peripheral tissues was made visually centered on an inflammatory reaction, etc. The remaining two rabbits were sacrificed with excessive anesthesia and after the peripheral tissue containing the implanted portion was extracted, ordinary formalin fixation was conducted and then a section was prepared, which was observed under a microscope.

From the results of these observations, the sample membrane showed no significant inflammatory reaction, etc. as compared with the control at any observation time for all rabbits, thus revealing that the adhesion-preventing membrane obtained by the present invention has good biocompatibility. In the case where 4 weeks elapsed from the implanting, it was observed that the sample membrane was decomposed and absorbed.

Example 10

Study of Adhesion Preventing Effect

Ten rats (body weight 250 g to 300 g) were divided into two groups each consisting of 5 rats, one group being a control and the other a sample group which used the adhesion-preventing membrane prepared in Example 6. For each of the control group and sample group, the rats were narcotized intramuscularly and thereafter the narcotized state was retained by inhalation anesthesia. For the control group, the rats were incised at the abdomen under anesthesia to expose the cecum and then the chorion of a size of about 5 mm square was peeled off. The abdominal portion corresponding to the cecum chorion was peeled off similarly and an adhesion model in which the injured surface of cecum and the injured abdominal surface served as connection surfaces was prepared. Thereafter, for the control group, the abdomen was stitched without any further treatment.

On the other hand, for the sample group, an adhesion model was prepared in the same manner as the control group and thereafter the injured cecum surface was covered with the adhesion preventing membrane prepared in Example 6 and fixed. The size of fixed adhesion preventing membrane was on the order of about 10 mm×10 mm and the membrane was sutured and fixed at the four corners thereof being lightly hung on the intestinal tract with a suture (5-0 bicryl thread). For both the sample group and the control group, the rats were reoperated after 4 weeks for celiotomy to visually observe the respective states of adhesion.

The degree of adhesion upon visual observation was judged based on the criteria in Table 2 above and assigned score to comparatively evaluate the sample group and control group. Rank 3 or higher was adopted for concluding that adhesion occurred.

As a result of comparative study between the sample: group and the control group based on these criteria, there was in the sample group no example case in which adhesion was observed while in the control group adhesion at Rank 3 or higher was observed for all cases. In the sample group, the adhesion preventing membrane remained at the fixed part but did not move to other parts for almost all of the cases so that it served to separate the injured surfaces from each other. Further, the adhesion preventing membrane which remained was carefully peeled off and the injured surface of the cecum was visually observed. As a result, it was observed that the injured surface healed. Detailed evaluation results with respect to the adhesion preventing effect are as shown in Table 5 below. Thus, it was shown that the adhesion preventing membrane of the present invention is effective in adhesion preventing effect and tissue regeneration effect.

TABLE 5

|  | Control group | Sample group |
| --- | --- | --- |
| Average score | 3 | 0.4 |
| Number of adhesion confirmed | 5 cases | 0 case |

As will be apparent from Table 5, the adhesion preventing membrane of the present invention has a cover layer of gelatin or hyaluronic acid over its surface so that it is excellent in adhesion preventing effect and tissue regenerating effect.

The adhesion preventing membrane of the present invention is excellent in suture strength, biocompatibility, induction of tissue regeneration and further has an adhesion-preventing property. Therefore, it is useful as an artificial biomembrane capable of preventing adhesion of an injured part or a bleeding part after operation, etc. or of adhesion of such parts with a normal part.

What is claimed is:

1. A suturable adhesion-preventing membrane for guided tissue regeneration comprising at least one non-woven fabric layer made of collagen fibers and at least one sponge layer made of collagen, characterized in that a surface of the membrane is provided with a coating layer of gelatin or hyaluronic acid.

2. A suturable adhesion-preventing membrane for guided tissue regeneration according to claim 1, wherein the coating layer containing gelatin or hyaluronic acid is a sponge or film.

3. A suturable adhesion-preventing membrane for guided tissue regeneration according to claim 1, wherein the coating layer containing gelatin or hyaluronic acid comprises cross-linked gelatin or hyaluronic acid.

4. A suturable adhesion-preventing membrane for guided tissue regeneration according to claim 1, wherein the coating layer containing gelatin or hyaluronic acid is formed by lyophilization.

5. A suturable adhesion-preventing membrane for guided tissue regeneration according to claim 1, wherein the coating layer containing gelatin or hyaluronic acid is a compressed sponge layer.

6. A suturable adhesion-preventing membrane for guided tissue regeneration according to claim 1, wherein the coating layer containing gelatin or hyaluronic acid has a thickness of 0.05 mm to 20 mm.

7. A suturable adhesion-preventing membrane for guided tissue regeneration according to claim 1, wherein the collagen of the collagen fibers and the collagen of the at least one sponge layer are independently selected from enzyme-solubilized collagen, acid-solubilized collagen, alkali-solubilized collagen or neutral solubilized collagen.

8. A suturable adhesion-preventing membrane for guided tissue regeneration according to claim 1, wherein a part or all of the collagen in the non-woven fabric layer made of collagen fibers comprises a cross-linked collagen.

9. A suturable adhesion-preventing membrane for guided tissue regeneration according to claim 1, wherein the non-woven fabric layer made of collagen fibers is obtained by coagulating collagen fibers which are extruded and crossed over in multiple folds, or extruded and wound on a plate in a certain direction to have paralleled lines of fibers, and compressing the coagulated fibers.

10. A suturable adhesion-preventing membrane for guided tissue regeneration according to claim 1, wherein the non-woven fabric layer made of collagen fibers is a layer in which the fibers are joined together using a binder comprised of solubilized collagen solution.

11. A suturable adhesion-preventing membrane for guided tissue regeneration according to claim 1, wherein the non-woven fabric layer made of collagen fibers has a thickness of 0.05 mm to 100 mm and the coating layer made of gelatin or hyaluronic acid has a thickness of 0.050 mm to 20 mm.

12. A suturable adhesion-preventing membrane for guided tissue regeneration according to claim 1, wherein the membrane is composed of a laminated membranous substance having one to six layers of the non-woven fabric layer made of collagen fibers.

13. A suturable adhesion-preventing membrane for guided tissue regeneration according to claim 1, wherein the collagen non-woven fabric layer has fibers having a fiber diameter of 5 $\mu$m to 1.0 mm, and a bulk density (fiber density) of $5 \times 10^{-4}$ to 5 g/cm$^3$.

14. A suturable adhesion-preventing membrane for guided tissue regeneration according to claim 1, wherein the overall thickness of the membrane is 0.1 mm to 50 mm.

* * * * *